United States Patent [19]

Mirkin

[11] 4,366,380
[45] Dec. 28, 1982

[54] METHOD AND APPARATUS FOR STRUCTURAL ANALYSIS

[76] Inventor: George Mirkin, 5514 Yarwell, Houston, Tex. 77096

[21] Appl. No.: 243,064

[22] Filed: Mar. 12, 1981

Related U.S. Application Data

[63] Continuation-in-part of Ser. No. 83,783, Oct. 11, 1979, abandoned.

[51] Int. Cl.³ ............................................ G01N 23/00
[52] U.S. Cl. .................................... 250/306; 250/307; 250/310; 350/3.66
[58] Field of Search ............... 250/306, 307, 310, 311, 250/396, 397, 398; 350/3.66

[56] References Cited

U.S. PATENT DOCUMENTS

| | | | |
|---|---|---|---|
| 3,745,812 | 7/1973 | Korpel | 350/3.66 |
| 4,109,966 | 8/1978 | Ersoy | 350/3.66 |

*Primary Examiner*—Bruce C. Anderson
*Attorney, Agent, or Firm*—Arnold, White & Durkee

[57] ABSTRACT

Apparatus for the non-destructive structural analysis of a solid object, the apparatus comprising: a laser pulse generating device to generate a laser beam pulse at a selected frequency for application to an input surface of an object to be analyzed to generate an elastic wave pattern in the object; a scanning electron microscope for scanning at a frequency which is a multiple of the laser beam pulse frequency, the generated wave pattern over an output surface of the object to provide an output signal; a control device for controlling operation of the scanning electron microscope in relation to the laser beam pulse to progressively vary the phase difference between the scanning frequency and the laser beam pulse frequency, and a processing device for processing such an output signal to allow generation of a representative signal representative of such a wave pattern at a preselected time instant; generating means for generating a composite signal from such a representative signal and from a reference signal derived from the laser pulse frequency; and a digital computer for processing such a composite signal to provide reconstruction means in the form of a digital hologram for reconstructing a representation of the object. The invention further extends to a corresponding method.

21 Claims, 3 Drawing Figures

METHOD AND APPARATUS FOR STRUCTURAL ANALYSIS

This application is a continuation-in-part application of my copending application Ser. No. 083,783 filed Oct. 11, 1979, abandoned.

This invention relates to a method and to an apparatus for the non-destructive structural analysis of a solid object.

Non-destructive structural analysis of solid objects, without damaging the objects, is becoming increasingly important for investigating material compositions, material structures, material defects, material homogeneity, and the like.

Many non-destructive techniques are more art than science and are often limited to giving qualitative information only.

A great deal of research has been concentrated on the use of ultrasonics as a means of detecting flaws since ultrasonic waves can retain information about a flaw in material even after travelling some distance between the flaw and a sensor for sensing the waves.

Initially attempts to quantify the results were based essentially on calibrating techniques against standard samples designed to provide a series of known reflection amplitudes. Because of the difficulties involved in preparing standard reference samples, these attempts were at best only partially successful.

To obtain more information a set of sensors could be used or scanning by means of a single sensor could be applied to record the pattern of scattered ultrasonic waves. This does, however, present an additional complication in that elastic waves in a solid have three possible polarizations.

The problem presented, therefore, is to deduce the structure of an object from the scattering pattern. Imaging would tend to be a solution if it can provide an accurate visual picture of the structure thereby obviating the need for theorists to solve complex mathematical problems from the scattering pattern.

These methods have a number of inherent problems which limit the extent to which the information obtained can be quantified. These problems are, inter alia, based on the difficulties involved in generating wave patterns with sufficient pin-point accuracy and consistency, in sensing the wave pattern mechanically with sufficient resolution, and in determining the wave pattern with sufficient accuracy and resolution from a continuously oscillating wave pattern.

In accordance with this invention, a method for the non-destructive structural analysis of a solid object, comprises: applying a wave-generating pulse at a selected frequency to an input surface of the object to generate an elestic wave pattern in the object; scanning the generated wave pattern over an output surface of the object with an electron beam scanning device in an evacuated chamber at a frequency which is a multiple of the wave-generating pulse frequency, to provide an output signal; controlling operation of the scanning device in relation to the wave-generating pulse and processing the output signal to generate a representative signal representative of the wave pattern at a preselected time instant; generating a composite signal from the representative signal and from a reference signal related to the wave-generating pulse; and processing the composite signal to provide reconstruction means for the reconstruction of a representation of the object.

Further, according to the invention there is provided apparatus for the non-destructive structural analysis of a solid object, the apparatus comprising: a pulse generating device to generate a pulse at a selected frequency for application to an input surface of an object to be analysed to generate an elastic wave pattern in the object; an electron beam scanning device for scanning in an evacuated chamber at a frequency which is a multiple of a generated pulse frequency, a generated wave pattern over an output surface of such an object to provide an output signal; a control device for controlling operation of the the scanning device in relation to the pulse generating device, and a processing device for processing such an output signal to allow generation of a representative signal representative of such a wave pattern at a preselected time instant; generating means for generating a composite signal from such a representative signal and from a reference signal related to a generated pulse frequency; and processing means for processing such a composite signal to provide reconstruction means for reconstructing a representation of such an object.

In an embodiment of the method of this invention, the representative signal may be generated by progressively varying the phase difference between the scanning frequency and the wave-generating pulse frequency, and by periodically processing the output signal at a constant time interval in relation to the wave-generating pulse frequency.

In a corresponding embodiment of the apparatus of the invention, the control device may be adapted to control operation of the scanning device in relation to the pulse generating device by progressively varying the phase difference between the scanning frequency and the pulse frequency, and the processing device may be adapted to generate a representative signal by processing such an output signal periodically at a constant time interval in relation to the pulse frequency.

Since the output signal is processed periodically at a constant time interval in relation to the wave generating pulse frequency, with the progressive variation of the phase difference between the scanning frequency and the wave generating pulse frequency, the representative signal will be generated from portions of the output signal provided by the scanning device representative of successive output surface zones being scanned.

Thus the representative signal will be representative of the wave pattern on the output surface at a preselected time instant.

It will be appreciated that the phase difference may be varied continuously or stepwise, and that the rate of variation or extent of stepwise variation, as the case may be, will determine the degree of resolution provided by the representative signal.

It will further be appreciated that the scanning frequency, which is a multiple of the pulse frequency, may readily be controlled to provide a frequency which is suitable for effective handling by the scanning device.

In an alternative embodiment of the invention to generate a representative signal representative of the wave pattern at a preselected time instant, the scanning rate may be varied progressively to achieve the same objective. It will be appreciated, however, that this will require further processing of the output signal to adjust the representative signal generated thereby in relation to the particular scanning rate at the time when the representative signal is generated.

In one embodiment of the invention the processing means may comprise optical processing means to provide reconstruction means in the form of an optical hologram.

In an alternative embodiment of the invention, the processing means may comprise a computer programmed to provide reconstruction means in the form of a computer hologram.

The computer may conveniently, for example, be programmed to provide a digital hologram thereby permitting effective computer elimination of extraneous noise and other interference producing influences.

A suitable computer may be selected from any one of numerous types which are conventional and available.

The apparatus may conveniently include a display module to provide a holograph from the hologram.

If desired, by means of conventional techniques, either an optical hologram or a computer hologram produced, may be utilized to reconstruct any required section of an object being analysed.

While any conventional type of ultrasonic pulse generating device may be employed for generating elastic wave patterns in objects, in an embodiment of the invention the pulse generating device may conveniently comprise a laser for generating a laser beam pulse.

A laser can provide the advantages of a sufficiently narrow beam pulse to provide accurate, pin-point application of the pulse thereby improving the capability of high resolution, and of accurate and effective frequency control.

The electron beam scanning device may be any conventional electron beam scanning device which has a sufficiently narrow electron beam to provide an appropriate degree of resolution to provide reconstruction means for effective reconstruction of a representation of an object being analysed.

Thus, for example, the scanning device may be in the form of an indirect scanning device such as, for example, a Vidicon electron tube. Such a Vidicon tube would conventionally require a transducer, a high vacuum or liquid with a high electrolyte content between the tube and an object being analysed.

In an alternative embodiment of the invention, the scanning device may be in the form of a scanning electron microscope which is housed within an evacuation chamber.

A scanning electron microscope can provide the advantage of an extremely narrow scanning electron beam to provide high resolution, and the advantage of direct scanning of an output surface of an object thereby reducing extraneous interference.

In an example of this embodiment of the invention the evacuation chamber may conveniently include a support of any conventional type for supporting an object to be analysed within the evacuation chamber.

In this example of the invention, to reduce pulse generation on an object interfering with the pressure in such an evacuated chamber, where the pulse generating device comprises a laser for generating a laser beam pulse, a beam conducting fibre may be included which extends sealingly through a wall defining the evacuation chamber to conduct the laser beam pulse directly to an object to be analysed.

Various types of scanning electron microscope are available which would be suitable for use in this invention.

Similarly, the control device, processing device and generating means of this invention may be of any conventional type.

The reference signal which is related to the pulse frequency may be generated or obtained by any number of conventional techniques.

Thus, for example, the reference signal may be obtained by dividing the wave generating pulse before it reaches an object to be analysed, by employing an energy transducer between an object to be analysed and the wave-generating pulse, by sensing electronic control of the pulse generating device, or the like.

The method may include the step of treating an output surface of an object to be analysed to reduce interference resulting from imperfections in the output surface.

Thus, for example, where the object is an object which is capable of being polished, the output surface may be polished.

Alternatively, or where an object to be analyzed is not capable of being polished sufficiently, the output surface of the object may be treated by coating the output surface with a coating layer. Such a coating layer may conveniently be polished after application thereof.

While various materials would be suitable for coating the output surface, the coating material may conveniently be selected from the group comprising metals and semi-metals.

Thus, for example, the coating material may be any suitable metal, or a semi-metal such as silicon, gallium, germanium, bismuth, or the like.

In a further embodiment of the invention, the output surface of an object to be analysed may be treated by associating an electrostatic layer with the output surface which is capable of responding electrostatically to a generated wave pattern to facilitate sensing of the wave pattern by the scanning device.

The electrostatic layer may conveniently be a metallic layer.

An electrostatic layer provides the advantage that the electrostatic charge can change rapidly without inertia in response to a generated wave pattern thereby providing an improved topographical effect and thus the capability for improved resolution.

While the method and apparatus of this invention may be employed for the qualitative structural analysis of solid objects, they are particularly suitable for the non-destructive quantitative structural analysis of solid objects.

While the method and apparatus of this invention can have various applications in regard to the quantitative structural analysis of solid objects, they can have particular application in regard to geological analysis, the analysis of various types of objects, components and structural components, and the like.

Embodiments of the invention are now described by way of example with reference to the accompanying drawings.

Figure 1:
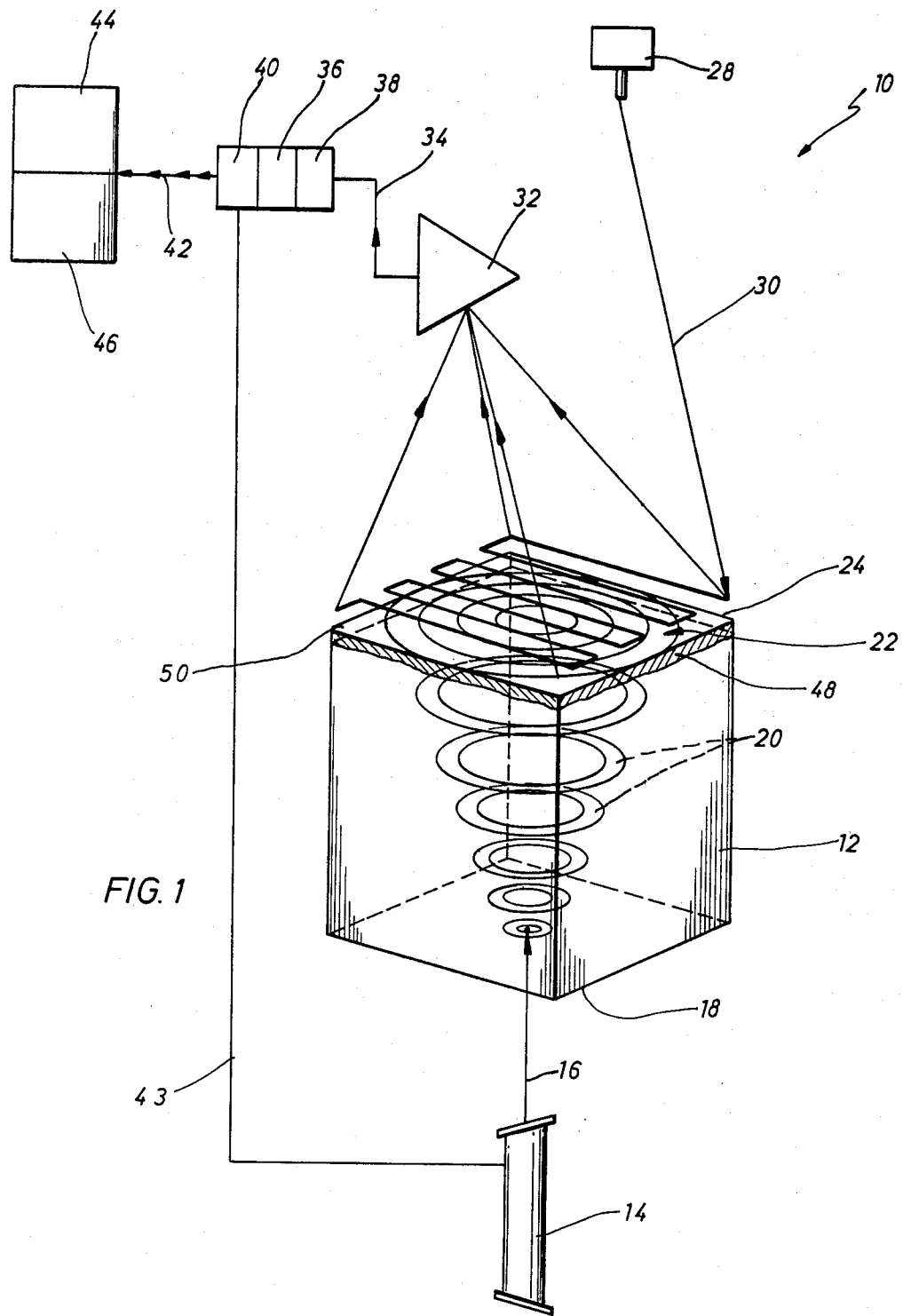
FIG. 1 shows a schematic representation of one embodiment of apparatus for the non-destructive quantitative structural analysis of a solid object.

With reference to FIG. 1 of the drawings, reference 10 refers generally to an apparatus for the non-destructive, quantitative, structural analysis of a solid object 12.

The apparatus 10 comprises a pulse generating device in the form of a laser 14 for generating a laser beam pulse 16 at a selected frequency for application to an input surface 18 of the object 12 to generate elastic waves 20 in the object and thus an elastic wave pattern 22 on an output surface 24 of the object 12.

The apparatus 10 further comprises an electron beam scanning device 26 for scanning the wave pattern 22. The conventional evacuated chamber for the electron beam device has been omitted from FIG. 1 for the sake of clarity.

The electron beam scanning device 26 comprises an electron beam generating device 28 for generating an electron beam 30 and causing the electron beam 30 to traverse the output surface 24 at a scanning frequency which is a multiple of the frequency of the laser beam pulse 16.

The scanning device 26 further comprises a sensor device 32 to sense the electrostatic response produced on the output surface 24 in response to the wave pattern 22 by the electron beam 30, and to produce an electrical output signal along an output line 34. The generated elastic waves 20 passing through the object 12 produce a topography or elastic wave pattern 22 on the output surface 24. The concentration of all electrons produced at the output surface 24 will be related directly to the surface topography produced by the elastic waves 20 and will determine the magnitude of the output signal produced by the sensor device 32.

The apparatus 10 further includes a control device 36 which is adapted to control operation of the scanning device 26 in relation to the laser 14 by progressively varying the phase difference between the scanning frequency and the pulse frequency, a processing device 38 for processing an output signal to allow generation of a representative signal representative of the wave pattern 22 at a preselected time instant, and generating means 40 for generating a composite signal 42 from such a respresentative signal and from a reference signal related to a generated pulse frequency. The control device 36, processing device 38 and generating means 40 are systems which are conventional and are known to persons of ordinary skill in the art. These systems may therefore readily be selected by persons of ordinary skill in the art from available systems and may then be adapted and associated in conventional manner to perform in accordance with this invention.

The control device 36 operates to synchronize the scanning frequency with the pulse frequency, and to vary the phase difference to permit generation of a representative signal representative of the generated wave pattern at a preselected time instant. Its operation can therefore readily be compared with, for example, that of a conventional controlling device for controlling the scanning coils in a conventional scanning electron microscope.

The reference signal is conveniently an electrical signal fed to the generating means 40 along the line 43, and generated in response to electronic control of the laser 14 to provide the laser beam pulse 16 of the required constant frequency.

The composite signal 42 is fed to either a computer 44 for generating a computer hologram or to an optical processor 46 for generating an optical hologram.

The computer hologram, or the optical hologram, as the case may be, is capable of reconstruction by conventional means to provide a holograph of the object 12. In addition, by conventional adjustment or focusing means, as the case may be, a holograph of any desired section of the object 12 may be provided.

While the control device 36 may be adapted to vary the phase difference continuously, it may conveniently be adapted to vary the phase difference stepwise between successive scanning operations or selected multiples of successive scanning operations.

The operation of the processing device 38 is such that for each variation of the phase difference by the control device 36, the processing device 38 will generate a reference signal during a scanning operation of the scanning device 26 at a constant time interval in relation to the frequency of the laser beam pulse 16.

The result will thus be that with the progressive variation of phase difference, the representative signal generated by the processing device 38 during a particular scanning traverse by the electron beam 30, will be representative of a surface zone in register with the electron beam 30 at that time instant.

It will be appreciated, therefore, that as the phase difference varies progressively, the particular surface zone of the output surface 24 in register with the electron beam 30 at the time instant when the representative signal is generated from the output signal will differ progressively since the representative signal is generated by periodically processinng the output signal at a constant time interval in relation to the laser beam pulse frequency.

In this way, the representative signal generated by the processing device 38 will represent the wave pattern 22 at a particular time instant, with the result that the wave represented by the complete representative signal will represent the wave pattern 22 as if it were in a standing or frozen state at the time interval selected.

It will be appreciated, therefore, that the processing device 38 combines storage of the set point data obtained by the electron beam scanning device 26, which is controlled by the control device 36, with an operation to distribute the data according to the coordinates and recesses of the wave scanning pattern. It is therefore of conventional type and may, for example, operate like an analog system (for example, a TV screen), or may operate like a digital system (such as a computer).

By providing a representative signal of the complete wave pattern 22 over the entire output surface 24 as if generated in a single instant of time, the substantial advantage can be provided of reducing, if not totally eliminating, the complex analysis problems presented by continuous oscillation of the wave patterns, thereby substantially facilitating analysis of the wave pattern and thus quantitative analysis of the structure of the object 12.

The generating means 40 compares the reference signal with the representative signal in accordance with conventional holographic techniques to provide a hologram for visual or other reconstruction of a representation of the object 12.

It will be appreciated that the generating means 40 operates purely as a conventional signal mixing device which is commonly referred to as a heterodyne.

In the case of an analog system the generating means 40 may be represented as a heterodyne which is connected to the processing device 38 and to the electronic control of the laser 14. In the case of a digital system the generating means 40 may operate like a computer program that distributes the reference data according to the coordinate addresses of the scanning pattern.

It will be appreciated that the resolution detail of the wave pattern 22 will depend upon and can effectively be controlled by the rate at which or degree by which the phase difference is progressively varied.

Therefore depending upon the degree of resolution required for a particular object 12, the rate of phase variation, or degree of successive phase variation may conveniently be controlled at a minimum to match the effective capability of the scanning device 26 thereby providing a resolution which is dependent upon the capacity of the scanning device 26.

In the embodiment illustrated in FIG. 1, the object 12 is, for example, an object such as a rock section which cannot provide a sufficiently smooth output surface, even after polishing, to avoid interference in the wave pattern 22 resulting from surface imperfections.

In this embodiment therefore, the output surface 24 is shown coated with a thin metallic or semi-metallic layer 48 which has a highly polished surface.

The coating layer 48 provides the advantage that it reduces interference resulting from possible imperfections in the output surface 24.

To improve the sensing capability of the scanning device 26, the polished surface of the coating layer 48 has an electrostatic layer 50 provided thereon.

While the electrostatic layer 50 may be a separate metallic layer provided on the coating layer 48, the coating layer 48 may conveniently be of a suitable metal to constitute both the coating layer 48 and the electrostatic layer 50.

The electrostatic layer 50 provides the advantage that it can respond electrostatically to the wave pattern 22 without intertia, thereby facilitating electrostatic interaction with the electron beam 30 and thus enhancing sensing of the wave pattern 22 by the sensor device 32.

Figure 2:
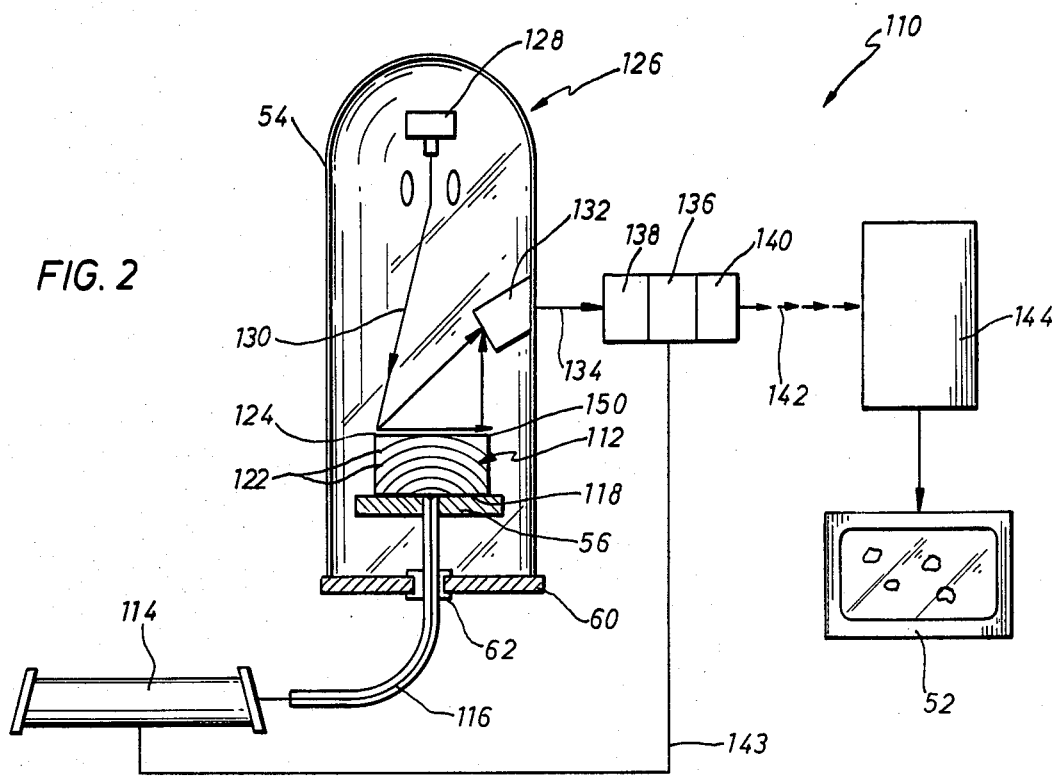
FIG. 2 shows a schematic representation of an alternative embodiment of the invention.

With reference to FIG. 2 of the drawings, reference 110 refers generally to an alternative embodiment of apparatus for the non-destructive quantitative structural analysis of a solid object 112.

The apparatus 110 corresponds substantially with the apparatus 10 and corresponding parts are indicated by corresponding reference numerals except that the reference numerals or FIG. 2 include a hundred prefix.

In the apparatus 110 the electron beam scanning device 26 comprises a scanning electron microscope, and the apparatus 110 includes a display module 52 for displaying a visual reconstruction of the object 112 or of a desired section of the object 112.

The scanning electron microscope 126 includes an evacuation chamber 54.

The evacuation chamber 54 includes a support 56 for supporting the object 112 within the evacuation chamber 54.

The apparatus 110 further includes a laser beam conducting fibre 58 for conducting the laser beam pulse 116.

The conducting fibre 58 may be of any conventional type, and extends sealingly through a base wall 60 defining the evacuation chamber 54.

Sealing is provided by a sealing sleeve 62.

The conducting fibre 58 extends through the support 56 into contact with the input surface 118 of the object 112.

This provides the advantage that the laser beam 116 can be applied directly to the input surface 118 within the evacuation chamber 54, thereby reducing interference which can result from indirect application of the laser beam pulse 116, and which can result from interference with the reduced pressure within the evacuation chamber 54 during use.

By locating the object 112 within the evacuation chamber 54, the high resolution and effective scanning capability of a scanning electron microscope, as compared to other conventional electron beam scanning devices, can be utilized in a particularly effective manner for effective and detailed quantitative analysis of the structure of the object 112.

The embodiment of the invention as illustrated in FIG. 2 of the drawings can therefore provide the advantages of effective utilization of a high resolution scanning electron microscope 126, together with the advantages of pin-point accuracy and control of a laser beam pulse applied directly to the input surface 118 thereby providing for accurate and effective quantitative analysis of the structure of the object 112.

The apparatus 110, as in the case of the apparatus 10, can provide the further advantage that by generating a representative signal representative of the wave pattern at a particular selected time instant, resolution is facilitated as also reconstruction of a representation of the object 112 with minimum interference due to the continuously oscillating movement of the generated wave pattern.

Figure 3:
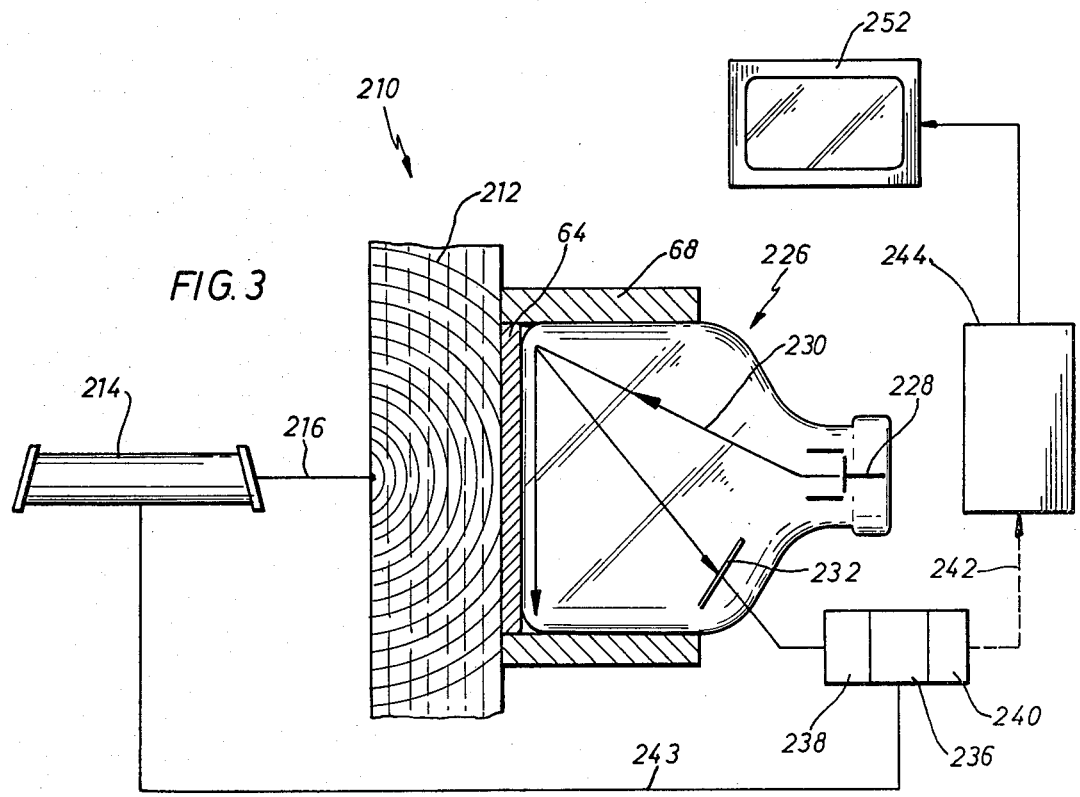
FIG. 3 shows a schematic representation of yet a further alternative embodiment of the invention.

With reference to FIG. 3 of the drawings reference 210 refers generally to yet a further alternative embodiment of apparatus in accordance with this invention.

The apparatus 210 corresponds generally with the apparatus 110. Corresponding parts are therefore indicated by corresponding reference numerals except that the prefix "2" is used in place of the prefix "1".

The apparatus 210 includes, as the electron beam scanning device 226, a Vidicon electron tube.

The Vidicon tube 226 is not able to scan the surface of the object 212 directly and therefore includes a suitable transducer 64 between the object 212 and the evacuation chamber 66 of the Vidicon tube 226.

The Vidicon tube 226 includes a housing sleeve 68 for locating the transducer 64 sealingly in position.

The apparatus 210 may be employed to analyse the structure of enlarged objects such as the object 212, by analysing selected portions of such objects.

The embodiment of the invention as illustrated in FIG. 3 can provide the advantage that after a particular portion of an object 212 has been analysed, the laser 214 and the Vidicon tube 226 can be moved in unison to analyse other selected portions of the object 212.

While the apparatus 210 has the disadvantage over the apparatus 110 in that it cannot provide the same degree of resolution and accuracy, it can nevertheless have application in relation to much larger objects 212 which require less critical structural analysis.

Insofar as the components of the apparatus of this invention are concerned, a suitable laser for use may conveniently be a laser of the type provided by Spectrophysics of the United States of America. The scanning electron microscope may conveniently be one of the type described in the catalogue of Coates and Welter (Record 106A SEM ultra high resolution, U.S.A. 4/1/75).

The control device may be of any conventional type. It may conveniently be a digital timer device controlled by a special program.

For the scanning electron microscope of the type described above, convenient sample ranges which can be employed would vary up to about ½" diameter samples.

I claim:

1. A method for the non-destructive structural analysis of a solid object, the method comprising:
   applying a wave-generating laser beam pulse at a selected frequency to an input surface of the object to generate an elastic wave pattern in the object;
   scanning the generated wave pattern over an output surface of the object with an electron beam scanning device in an evacuated chamber at a frequency which is a multiple of the wave-generating pulse frequency, to provide an output signal;
   controlling operation of the scanning device in relation to the wave-generating pulse and processing the output signal to generate a representative signal representative of the wave pattern at a preselected time instant;
   generating a composite signal from the representative signal and from a reference signal related to the wave-generating pulse; and
   processing the composite signal to provide reconstruction means for the reconstruction of a representation of the object.

2. A method according to claim 1, in which the representative signal is generated by progressively varying the phase difference between the scanning frequency and the wave-generating pulse frequency, and by periodically processing the output signal at a constant time interval in relation to the wave-generating pulse frequency.

3. A method according to claim 1 or claim 2, in which the composite signal is processed to provide reconstruction means in the form of an optical hologram of the object.

4. A method according to claim 1 or claim 2, in which the composite signal is processed by means of a computer programmed to provide reconstruction means in the form of a computer hologram of the object.

5. A method according to claim 4, in which the computer is programmed to provide a digital hologram of the object.

6. A method according to claim 5, in which a display module is associated with the computer to provide a holograph of the object from the digital hologram.

7. A method according to claim 1 or claim 2, which includes the step of coating the output surface of the object with a coating layer to reduce interference resulting from imperfections in the output surface.

8. A method according to claim 7, in which the output surface is coated with a material selected from the group consisting of metals and semi-metals.

9. A method according to claim 1 or claim 2, which includes the step of associating an electrostatic layer with the output surface, the electrostatic layer being capable of responding electrostatically to the wave pattern to facilitate sensing of the wave pattern by the scanning device.

10. A method according to claim 1 or claim 2, in which the scanning device is in the form of a scanning electron microscope housed within an evacuation chamber.

11. A method according to claim 10, in which the object is sealed within the chamber.

12. A method according to claim 11, in which the laser beam pulse is transmitted to the input surface by means of a beam conducting fibre which passes sealingly through a wall defining the chamber.

13. Apparatus for the non-destructive structural analysis of a solid object, the apparatus comprising:
    a laser pulse generating device to generate a laser beam pulse at a selected frequency for application to an input surface of an object to be analysed to generate an elastic wave pattern in the object;
    an electron beam scanning device for scanning in an evacuated chamber at a frequency which is a multiple of a generated pulse frequency, a generated wave pattern over an output surface of such an object to provide an output signal;
    a control device for controlling operation of the the scanning device in relation to the pulse generating device, and a processing device for processing such an output signal to allow generation of a representative signal representative of such a wave pattern at a preselected time instant;
    generating means for generating a composite signal from such a representative signal and from a reference signal related to a generated pulse frequency; and
    processing means for processing such a composite signal to provide reconstruction means for reconstructing a representation of such an object.

14. Apparatus according to claim 13, in which the control device is adapted to control operation of the scanning device in relation to the pulse generating device by progressively varying the phase difference between the scanning frequency and the pulse frequency, and in which the processing device is adapted to generate a representative signal by processing such an output signal periodically at a constant time interval in relation to the pulse frequency.

15. Apparatus according to claim 13 or claim 14, in which the processing means comprises optical processing means to provide reconstruction means in the form of an optical hologram.

16. Apparatus according to claim 13 or claim 14, in which the processing means comprises a computer programmed to provide reconstruction means in the form of a computer hologram.

17. Apparatus according to claim 16, in which the computer is programmed to provide a digital hologram.

18. Apparatus according to claim 17, including a display module to provide a holograph from the digital hologram.

19. Apparatus according to claim 13 or claim 14, in which the scanning device is in the form of a scanning electron microscope housed within an evacuation chamber.

20. Apparatus according to claim 19, in which the evacuation chamber includes a support for supporting an object to be analysed within the evacuation chamber.

21. Apparatus according to claim 20, in which the apparatus includes a beam conducting fibre which extends sealingly through a wall defining the evacuation chamber, and which extends to the support.

* * * * *